United States Patent
Shan et al.

(10) Patent No.: US 11,173,316 B2
(45) Date of Patent: Nov. 16, 2021

(54) METHOD OF MANUFACTURING AN IMPLANTABLE DEFIBRILLATION COIL

(71) Applicant: SORIN CRM SAS, Clamart (FR)

(72) Inventors: Nicolas Shan, Juvisy sur Orge (FR); Philippe D'Hiver, Chatillon (FR); Aaron Romo, Clichy (FR)

(73) Assignee: Sorin CRM SAS, Clamart (FR)

( * ) Notice: Subject to any disclaimer, the term of this patent is extended or adjusted under 35 U.S.C. 154(b) by 812 days.

(21) Appl. No.: 15/760,625

(22) PCT Filed: Sep. 21, 2016

(86) PCT No.: PCT/IB2016/055647
§ 371 (c)(1),
(2) Date: Mar. 15, 2018

(87) PCT Pub. No.: WO2017/051336
PCT Pub. Date: Mar. 30, 2017

(65) Prior Publication Data
US 2018/0256910 A1 Sep. 13, 2018

(30) Foreign Application Priority Data
Sep. 22, 2015 (FR) ..................................... 1558905

(51) Int. Cl.
*A61N 1/39* (2006.01)
*A61N 1/05* (2006.01)

(52) U.S. Cl.
CPC ......... *A61N 1/3968* (2013.01); *A61N 1/0563* (2013.01); *A61N 1/3956* (2013.01)

(58) Field of Classification Search
CPC ... A61N 1/3968; A61N 1/3956; A61N 1/0563
See application file for complete search history.

(56) References Cited

U.S. PATENT DOCUMENTS

| | | | |
|---|---|---|---|
| 4,934,049 A * | 6/1990 | Kiekhafer | A61N 1/056 29/605 |
| 5,115,818 A * | 5/1992 | Holleman | A61N 1/056 607/122 |
| 5,776,165 A | 7/1998 | Ripart | |

(Continued)

FOREIGN PATENT DOCUMENTS

| | | |
|---|---|---|
| EP | 0 442 444 A2 | 8/1991 |
| EP | 0 773 039 A1 | 5/1997 |

OTHER PUBLICATIONS

International Search Report and Written Opinion for International Patent Application No. PCT/IB2016/055647, dated Jan. 9, 2017, 10 pages.

*Primary Examiner* — Catherine M Voorhees
(74) *Attorney, Agent, or Firm* — Foley & Lardner LLP (57) ABSTRACT

The disclosure relates to a method of manufacturing an implantable defibrillation coil for a lead of an active implantable medical device, the defibrillating coil includes at least one elongate conductive coil which includes a plurality of non-contiguous turns. The method includes inserting a tube of polymeric material within the elongated conductive coil, supplying thermal energy to soften the tube, applying pressure on the assembly formed by the elongate conductive coil and causing the tube to deform the tube wall by insertion of the tube wall between the turns of the elongate conductive coil.

8 Claims, 5 Drawing Sheets

(56) References Cited

U.S. PATENT DOCUMENTS

| | | | |
|---|---|---|---|
| 2006/0241734 A1* | 10/2006 | Marshall | A61N 1/0563 607/122 |
| 2010/0137958 A1* | 6/2010 | Seifert | A61N 1/0563 607/116 |
| 2010/0137959 A1 | 6/2010 | Seifert | |

* cited by examiner

-Prior Art-

Figure 1

-Prior Art-

METHOD OF MANUFACTURING AN IMPLANTABLE DEFIBRILLATION COIL

CROSS-REFERENCE TO RELATED PATENT APPLICATIONS

This present application is a 371 U.S. National Application of International Application No. PCT/IB2016/055647, filed Sep. 21, 2016, which claims the benefit of and priority to French Patent Application No. 1558905, filed Sep. 22, 2015, which is incorporated herein by reference in its entirety.

FIELD OF THE INVENTION

The disclosure generally relates to "active implantable medical devices" as defined by the Directive 90/385/EEC of 20 Jun. 1990 of the Council of the European Communities.

More particularly, the disclosure relates to the family of devices able to terminate tachyarrhythmias by delivering a shock to the heart in the form of electrical pulses of high energy significantly exceeding the level required for a simple stimulation.

BACKGROUND

These devices are generally named implantable cardioverters/defibrillators or ICDs.

The devices consist of two elements, a pulse generator and a lead or a system of leads.

The generator is for monitoring heart activity and for generating high-energy pulses when the heart presents a ventricular arrhythmia that may be treated by the application of a defibrillation shock.

When the energy is between 0.1 and 10 Joules, this therapy is designated as "cardioversion" and the electrical shock is called a "cardioversion shock." When this energy is greater than 10 Joules, the electric shock is then called "defibrillation shock." However, in the remainder of the present description, the term defibrillation will be used both to designate cardioversion and defibrillation.

EP 0773039 A1 and its U.S. counterpart U.S. Pat. No. 5,776,165 (ELA Medical) describes a generator/lead system, with means to choose the optimum configuration for the application of defibrillation shock.

The disclosure specifically relates to the defibrillation coils for leads of active implantable medical devices to deliver the defibrillation shock.

Figure 1:
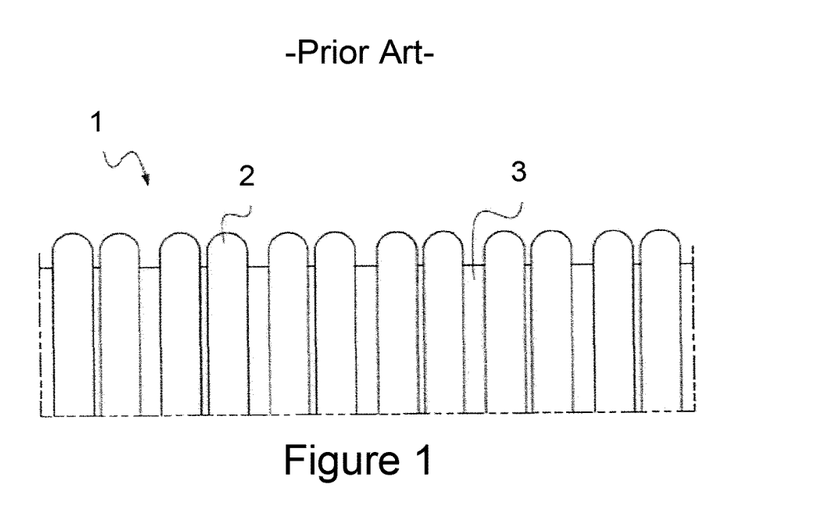
FIG. 1 shows a defibrillation coil having gaps between the turns of the coil.

A defibrillation coil 1 is in the form of a conductive material 2 mounted on an insulating material 3 as shown in FIG. 1, intended to come into contact with tissue at the place where the defibrillation energy is to be applied. The defibrillation coil is connected to a conductor wire traversing the lead along its length up to the corresponding terminal of the connector at the proximal end.

These leads usually include two defibrillation coils, i.e. a defibrillation coil called "supraventricular" coil, which is positioned in the superior vena cava to apply shock to the atrium, and a second defibrillation, ventricular, coil located within the right ventricle of the heart, closer to the distal end of the lead.

The "supraventricular" defibrillation coil has a length of about 8 cm and a surface of about 500 $mm^2$. The ventricular defibrillation coil has a length of 5 cm and about 300 $mm^2$ surface.

To be effective, the defibrillation coils must have a large surface area exposed to heart tissue and/or endovascular.

However, the defibrillation coil in contact with the interior of the human body causes an immune reaction against the implanted foreign body.

The immune response may be reduced by using biocompatible material. However, the use of biocompatible material does not eliminate the immune reaction.

The immune reaction of the human body causes fibrotic tissue growth around the defibrillation coil to encapsulate the coil, in particular the conductive material.

The development of this fibrotic tissue is particularly concentrated in the space between the turns of the defibrillation coil that are close or in direct contact with the surrounding tissue.

This undesirable development of fibrotic tissue raises many problems.

First, the presence of fibrotic tissue between the turns of the coil and the cardiac tissue causes a decrease in electrical conductivity between the coil and the heart tissue.

Then the fibrotic tissue connecting the coil defibrillation to the cardiac and/or endovascular tissue, it becomes difficult or impossible to simply remove the coil without using specific tools and without damaging tissues or organs located near the assembly formed by the fibrotic tissue and the defibrillation coil.

Figure 2:
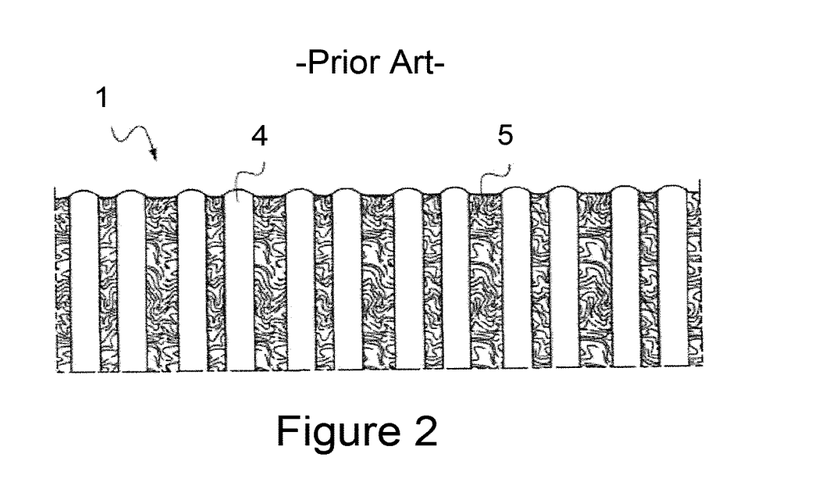
FIG. 2 shows a defibrillation coil with a filling space between the turns of the coil.

To solve this problem, it is common to fill the existing gap between each turn 4 of the defibrillation coil 1 with an insulating plastic material 5 as shown in FIG. 2.

Filling the existing empty space between the turns of the defibrillation coil is performed to minimize the empty space between the turns, minimizing the cavities present between the turns minimizes the development of fibrotic tissue. Indeed, it has been observed that the development of fibrotic tissue takes place in the cavities formed by the empty spaces between the turns.

In addition, filling the space between the turns of the defibrillation coil is performed to provide good mechanical stability to the defibrillation coil while keeping the isodiametry of the coil, such that the coils have the same diameter throughout their length. The isodiametry of the defibrillation coils facilitates implantation into the venous system, and a subsequent explantation. In other words, according to this feature, the outer surface of the coils shall show no diameter changes throughout the implanted length.

Finally, the filling must be executed without covering the surface of the turns of the defibrillation coil in contact with the cardiac and/or endovascular tissue. Covering the surface would reduce the effectiveness of the defibrillation coil. The surface of the defibrillation coil must be directly exposed to the cardiac and/or endovascular tissue in order to ensure an optimal application of the therapy to be applied to the patient. Thus, the filling should cover the non-functional surface of the turns of the coil, the side of the turns, while keeping the outer surface of the functional turns.

Several manufacturers have implemented manufacturing methods of defibrillation coil with filling of the space between the turns of the defibrillation coil. In particular, it is common to use silicone to fill these spaces. After filling, excess silicone is cleaned.

These methods have drawbacks. First, the filling of the spaces between the turns of the defibrillation coils is irregular along the coil thereby leaving cavities conducive to the development of fibrotic tissue. In addition, the diameter of the coil after application of the filling is not constant. The drawbacks explained above are thus still present. Finally, cleaning may leave particles which have tendencies to be released after implantation of the defibrillation coil in the patient's body.

The use of an external polymer coating to the defibrillation coil is also known. However, this solution has drawbacks, in particular the external polymer increases the rigidity and the thickness of the defibrillation coil and reduces the efficiency of the defibrillation coil during application of a defibrillation shock.

One of the aims of the present disclosure is to remedy these drawbacks by proposing a manufacturing method of a defibrillation coil, which does not have any cavity area between the turns of the defibrillation coil and moreover, can be simply and quickly manufactured.

SUMMARY

The present disclosure provides a method of manufacturing an implantable defibrillation coil for a lead of an active implantable medical device, the defibrillating coil comprising at least one elongate conductive coil comprising a plurality of non-contiguous turns.

The method comprises:
A step of inserting a tube made of polymer material inside the elongated conductive coil,
A thermal energy input step to soften the tube,
A step of applying pressure on the assembly formed by the elongate conductive coil and the tube to deform the tube wall by insertion of the tube wall between the turns of the elongate conductive coil.

According to various embodiments:
The step of applying pressure includes applying a pressure within the tube after insertion of the tube into the elongate conductive coil.
The thermal energy input step is to apply an electric current to the elongate conductive coil for creating thermal energy.
The application of electric current to the elongate conductive coil comprises a prior step of positioning an electrical connection substantially at each end of the elongate conductive coil.
The method further comprises a step of positioning the elongate conductive coil after the insertion of the tube into the elongate conductive coil in a tubular mold (110) of a diameter substantially equal to the outer diameter of the elongated conductive coil.
The applying pressure step includes applying a radial compressive force applied to the outer surface of the assembly formed by the elongate conductive coil and the tube.
The thermal energy input step is to apply external heat energy.
The polymer material of the tube is polyurethane.
The outside diameter of the tube is substantially smaller than the inside diameter of the elongate conductive coil.
The outside diameter of the tube is substantially greater than or equal to the inner diameter of the elongate conductive coil.

The disclosure also relates to an implantable defibrillation coil for a lead of an active implantable medical device, the defibrillating coil comprising at least one elongate conductive coil comprising a plurality of non-contiguous turns. The defibrillation coil comprises a tube made of polymer material having corrugations between the turns of the elongated conductive coil, the defibrillation coil being obtained according to the manufacturing method described above.

BRIEF DESCRIPTION OF THE DRAWINGS

Further features, embodiments and advantages of the present disclosure will become apparent to a person of ordinary skill in the art from the following detailed description of embodiments of the present disclosure, made with reference to the drawings annexed, in which like reference characters refer to like elements and in which.

DETAILED DESCRIPTION

Figure 3:
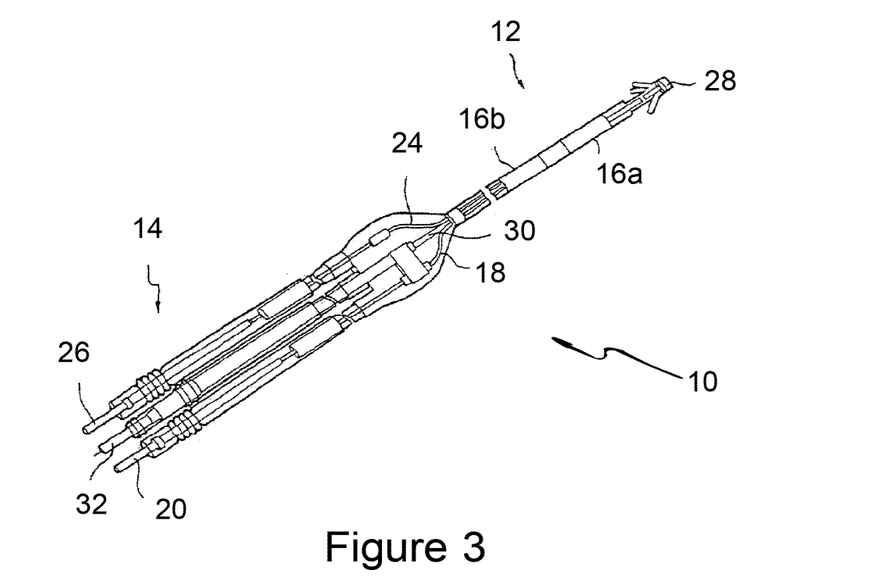
FIG. 3 shows an implantable lead comprising two defibrillation coils.

In FIG. 3, reference 10 generally indicates a lead, the distal portion 12 of which is intended to be introduced through the venous network in both the atrial and ventricular cavities, to apply, a defibrillation shock. This lead is provided at its proximal end 14 various connection elements to a suitable generator.

The lead 10 has a first defibrillation coil 16a, intended to be placed in the right ventricle and creating, for example, the negative terminal of application of the defibrillation potential. This ventricular defibrillation coil is connected by a connecting conductor 18 to a terminal 20 for connection to the generator, preferably a terminal compliant with the DF-1 or DF-4 standard.

The lead 10 also carries on its distal portion 12 a second defibrillation coil 16b, which is a "supraventricular" electrode intended to be positioned in the superior vena cava for applying a shock to the atrium; this supraventricular electrode 16b is connected by another conductor 24 to another terminal 26 for connection to the generator, also compliant with the DF-1 or DF-4 standard.

The lead 10 is also provided with a tip electrode 28, which is a detection/stimulation electrode to be positioned at the bottom of the right ventricular cavity. This electrode 28 is connected by a conductor 30 to a terminal 32 connecting the pacemaker, preferably compliant with the IS-1 standard.

The defibrillation potential can be applied between the supraventricular defibrillation coil 16b and the housing of the generator, or between the ventricular defibrillation coil 16a and the housing of the generator, or between the two defibrillation coils 16a and 16b.

However, the configuration that has just been described (two coils defibrillation) is however not limiting, and the disclosure is also well applicable in the case of a lead provided with a single defibrillation coil or comprising two, or more, defibrillation coils.

The method of manufacturing an implantable defibrillation coil 16 for a lead of an active implantable medical device 10 according to the disclosure, for example as illustrated in FIGS. 5 to 8, will now be described.

Such an implantable defibrillation coil 16 includes at least one elongate conductive coil 51 comprising a plurality of non-contiguous turns 52.

The conductor forming the elongate conductive coil may have a circular or a rectangular cross section and is made of a biocompatible material. However, other forms of the conductor section may also be considered, for example, ovoid, triangular, trapezoidal, etc.

The method of manufacturing a defibrillation coil 16 of the disclosure includes filling the empty space between the turns 52 of the elongate conductive coil 51 with an electrically insulating material 53.

The insulating material is a polymer material, such as polyurethane, for example Tecothane, Pellethane or other polyurethane.

The method for producing a defibrillation coil 16 according to the disclosure is based on the insertion of a tube 53 of a polymeric material within the elongate conductive coil 51, the use of thermal energy and the application of pressure to the assembly formed by the elongate conductive coil and the tube to deform the tube by insertion of the tube walls in the spaces between the turns 52 of the elongate conductive coil 51.

In particular, there is thermo-forming of the tube 53 which is softened by heat energy by shaping the tube wall between the turns 52 of the elongate conductive coil 51.

The polymer tube hardens again when cooled, while maintaining the shape given by the filling of the spaces between the turns of the elongated conductive coil.

By filling in the polymer tube spaces between each turn of the defibrillation coil, the capacity of fibrotic tissue that may anchor on and between the turns of the coil is minimized.

In addition, the use of a polyurethane tube for filling the spaces between the turns of the elongated conductive coil allows good mechanical stability of the defibrillation coil to be obtained, in particular when introduced into the venous system and at crossing of an introducer valve.

According to some embodiments, the thermal energy is obtained by passing a direct current along the elongated conductive coil 51.

Due to the electrical resistance of the elongated conductive coil, the electrical current imposed is transformed into thermal energy.

Alternatively or additionally, heat energy may be obtained by an external source.

This thermal energy is used to soften the tube wall of polymer.

The use of thermal energy to soften the polymeric tube in conjunction with the application of a pressure applied to the assembly formed by the elongate conductive coil and the soft tube, for example inside of the tube, allows the insertion of the tube wall between the turns of the elongated conductive coil and thus filling the empty space between the turns of the elongate conductive coil.

Figure 4:
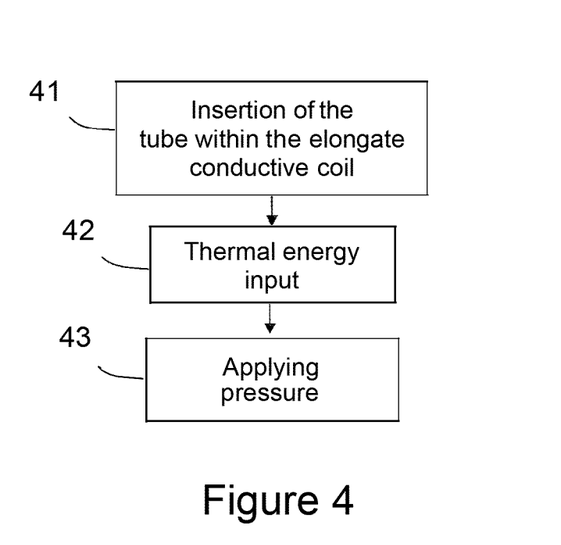
FIG. 4 shows a diagram of the method for producing a defibrillation coil according to the invention.

The method for manufacturing a defibrillation coil according to the disclosure is detailed below. FIG. 4 illustrates the steps of this method.

The manufacturing method includes a first step 41 of inserting a tube 53 into the polymer material within the elongate conductive coil 51.

In some embodiments, the outer diameter of the tube is substantially smaller than the inside diameter of the elongated conductive coil, such that upon inserting the tube it is in contact with the elongate conductive coil.

In some embodiments, the outer diameter of the tube is substantially greater than or equal to the inner diameter of the elongate conductive coil. According to this embodiment, the tube is force-fitted within the elongated conductive coil, contact occurs between the tube and the elongate conductive coil.

Figure 5:
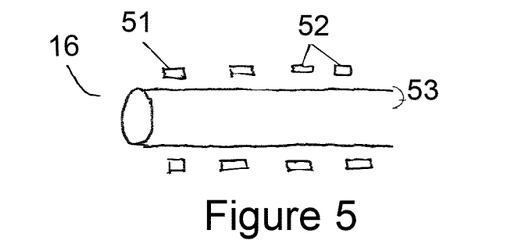
FIG. 5 illustrates an elongate conductive coil including a tube.

FIG. 5 illustrates the step of inserting the tube within the elongate conductive coil.

Step 41 is followed by a step 42 of using thermal energy to soften the tube.

The thermal energy can be achieved according to some embodiments by external thermal energy, for example, by insertion of the assembly formed by the elongate conductive coil and the tube in a heating device, such as an oven.

According to some embodiments of the thermal energy input step, an electric current is applied to the elongate conductive coil 51 to create a thermal energy to soften the tube.

The elongate conductive coil 51 is made of an electrically conductive material, so the application of electric current causes generation of thermal energy.

In order to apply an electric current to the elongate conductive coil, the method may include a step of positioning an electrical connection substantially at each end of the elongated conductive coil, or close to each end.

An electric current i may be applied during a specified period in order to soften the tube inserted into the elongated conductive coil.

Figure 6:
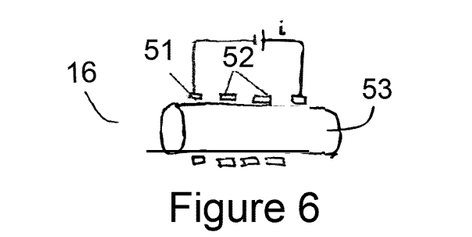
FIGS. 6, 7 and 8 illustrate different steps of manufacturing a defibrillation coil according to the invention.

This step is illustrated in FIG. 6.

According to some embodiments, the energy input can be accomplished by the introduction of external heat energy and by applying an electric current to the elongate conductive coil.

Step 42 is followed by a step 43 of applying a pressure on the assembly formed by the elongate conductive coil and the tube 53 to deform the tube wall by insertion of the wall between the turns 52 of the elongated conductive coil 51.

According to some embodiments, a pressure is applied within the tube 53 after insertion of the tube into the elongate conductive coil.

Figure 7:
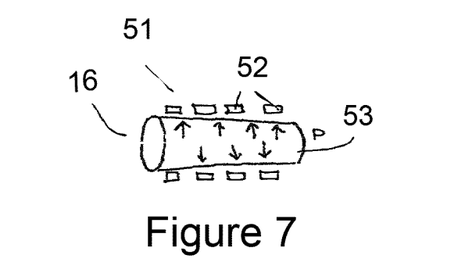

As shown in FIG. 7, a pressure may be applied on the inner wall of the tube so as to cause a deformation of the wall and the insertion of the wall between the coils of the elongate conductive coil.

Some embodiments also have the advantage of applying pressure to the tube wall so that the wall is brought into contact with the elongate conductive coil.

According to some embodiments for producing a defibrillation coil, a tubular mold of a diameter substantially equal to the outer diameter of the elongated conductive coil may be used to position the elongate conductive coil 51 after insertion of the tube 53 in the coil.

This embodiment is described with reference to FIGS. 11 and 12.

The mold serves to control the insertion of the tube in the spaces between the turns of the elongated conductive coil without exceeding the outer diameter of the elongate conductive coil.

According to some embodiments, a radial compression force P is applied on the outer surface of the assembly formed by the elongate conductive coil and the tube.

The radial compression force allows control of the insertion of the tube in the spaces between the turns of the elongated conductive coil so that this insertion does not create a cavity on the outer portion of the defibrillation coil and to have an isodiametric defibrillation coil.

Figure 8:
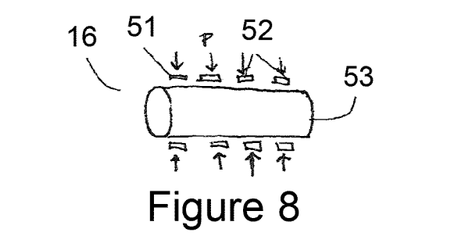

This embodiment is illustrated in FIG. 8.

According to some embodiments, a pressure is applied to the inside the tube and a radial compression force P is applied to the external surface.

It should be noted that the steps of bringing thermal energy 42 and applying a pressure 43 may be executed sequentially or in parallel.

Similarly, the step of applying a pressure 43 may be applied prior to the step of bringing thermal energy 42 and may continue during the step of applying or creating thermal energy.

In addition, the pressure applied in step 43 may continue through the cooling period of the tube so that the shaping of the tube wall between the turns of the elongated conductive coil is maintained until the tube reaches its initial rigidity level.

Figure 9A:
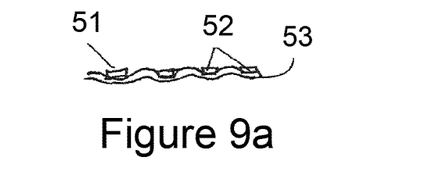
FIGS. 9a, 9b and 9c show the insertion of the wall between the turns of the elongated conductive coil after application of the method of manufacturing a defibrillation coil of the invention.
Figure 9B:
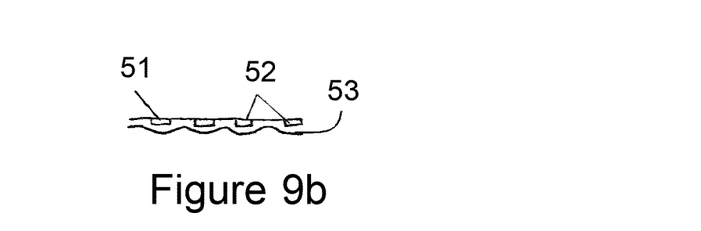
Figure 9C:
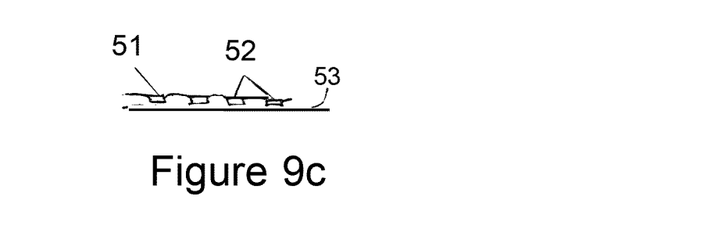

FIGS. 9a, 9b and 9c illustrate various results obtained by applying the method for producing a defibrillation coil according to the invention The filling of spaces between the turns 52 of the elongate conductive coil 51 by insertion of the wall of the tube 53 between the turns is illustrated in these figures.

Figure 10:
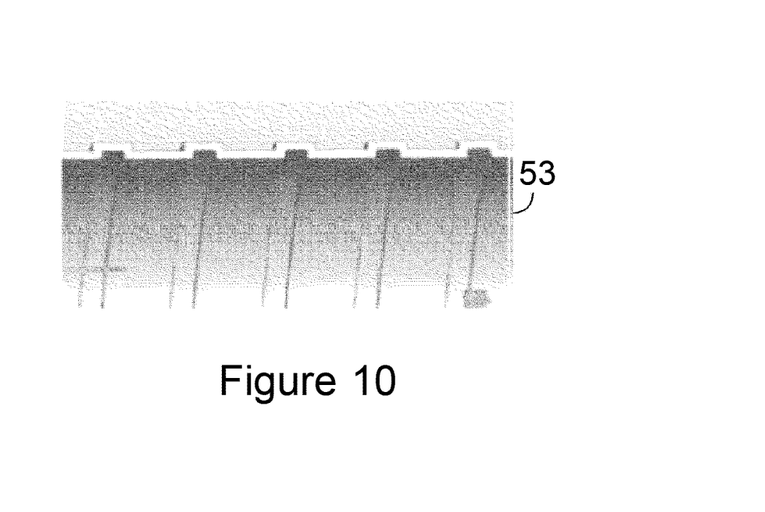
FIG. 10 shows a tube after insertion thereof between the turns of an elongate conductive coil.

In FIG. 9b, the result of the filling when using a mold is shown. According to this embodiment, the corrugations of the tube are created as illustrated in FIG. 10, this geometry allows flexibility of the defibrillation coil, simplifying its implantation.

FIG. 9c is the result of an embodiment using a tube having a large thickness of material.

The method for producing a defibrillation coil according to embodiments of the disclosure enables the production of a low-cost coil. Furthermore, since no cavity is created between the turns of the elongated conductive coil, no fibrotic tissue can be anchored. In addition, this method allows the manufacture of defibrillation coils having great flexibility due to the insertion of the tube into the spaces of the turns of the elongated conductive coil, a controlled insertion by application of the method of at least one force inside the tube, or also by one radial compressive force applied on the outer surface of the assembly formed by the elongate conductive coil and the tube. Finally, the manufacturing method according to the disclosure is easy to implement. This method applies a certain amount of current in a given time and/or provides a supply of thermal energy from an external source and applies one or several particular pressures. This method can be repeated and is therefore easily industrializable.

An exemplary embodiment of the method for producing a defibrillation coil according to the disclosure is now described using a tubular mold. This exemplary embodiment is illustrated in FIGS. 11 and 12.

Figure 11:
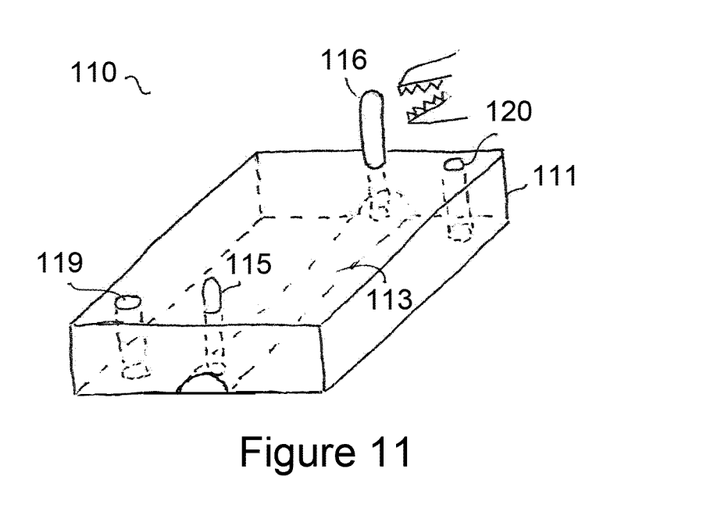
FIG. 11 is a representation of the upper part of a tubular mold.
Figure 12:
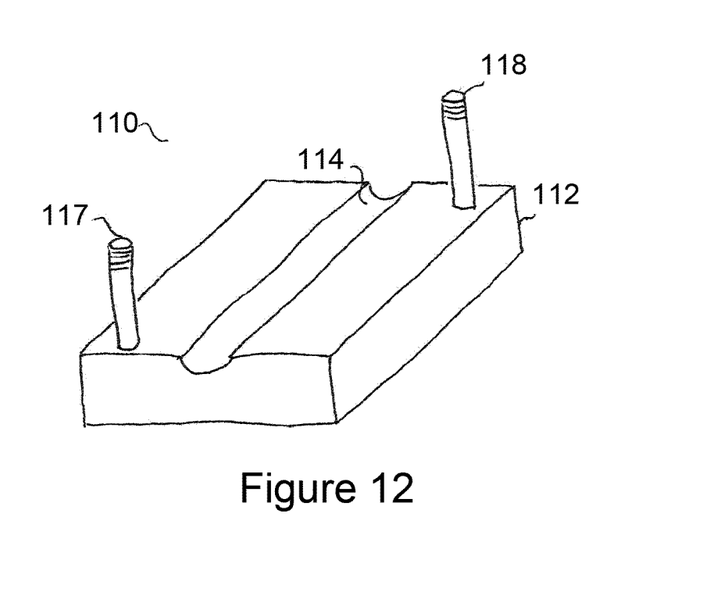
FIG. 12 is a representation of the lower part of a tubular mold.

According to this exemplary embodiment, the tubular mold 110 is formed in two parts 111 and 112, the upper part 111 being illustrated in FIG. 11 and the lower part 112 being illustrated in FIG. 12.

The upper 111 and lower 112 parts each comprise a groove, respectively 113 and 114, adapted to accommodate the elongate conductive coil within which a polymer tube is inserted. The grooves 113 and 114 form a tube of a diameter substantially equal to the outer diameter of the elongate conductive coil.

The upper part 111 of the tubular mold comprises two connection means 115 and 116 positioned substantially at each end of the groove 113, for example, positioned proximate each end of the groove 113, so as to be connected at each end of the elongate conductive coil when the latter is positioned in the groove. An amount of current is applied to these connection means to be transmitted to the elongate conductive coil inserted into the groove.

The lower part 112 of the tubular mold comprises two clamping means 117 and 118 adapted to be inserted in respective holes 119 and 120 of the upper part 111 of the tubular mold.

The upper end of the clamping means allows positioning a nut for clamping the two portions of the tubular mold and thus assembling the two parts of the mold.

The grooves 113 and 114 have an opening at both ends so as to form the inputs to a pressure device when the two parts are assembled.

Thus, to make a defibrillation coil, an elongate conductive coil and a polymer tube is first cut to the desired length according to production of a defibrillation supraventricular coil or the manufacture of a ventricular defibrillation coil.

Then, the tube is inserted inside the elongate conductive coil.

The assembly formed of the elongated conductive coil and the tube is then positioned on the lower portion 112 of the tubular mold and the upper mold 111 is assembled. The clamping means 117 and 118 maintain the assembly.

A current is applied to the connection means 115 and 116 connected to the elongate conductive coil.

A pressure is applied inside the tube by the openings formed by the grooves, the openings allowing accommodation of a pressure device.

The current applied on the connection means is applied during a given time and a given pressure is applied inside the tube. In this way, the tube softens and deforms the wall by insertion thereof between the coils of the elongate conductive coil.

The defibrillation coil obtained according to the method described is then integrated in the implantable defibrillation lead, the manufacturing of the lead providing an external isodiametry.

The defibrillation coil thus obtained has a stable and homogeneous structure preventing irregularities and thus reducing the anchorage capacity of fibrotic tissue.

What is claimed is:

1. A method of making an implantable defibrillation coil for a lead of an active implantable medical device, the implantable defibrillation coil comprising an elongated conductive coil comprising a plurality of non-contiguous turns, the method comprising:
    inserting a tube of polymer material within the elongated conductive coil;
    softening the tube by applying an electric current to the elongated conductive coil to create thermal energy; and
    applying a pressure on an assembly formed by the elongated conductive coil and the softened tube to deform a wall of the softened tube so that the tube wall goes between the plurality of non-contiguous turns of the elongated conductive coil.

2. The method of claim 1, wherein applying the pressure comprises applying a pressure within the tube after insertion of the tube into the elongated conductive coil.

3. The method of claim 1, wherein the application of electric current to the elongated conductive coil comprises positioning an electrical connection substantially at each end of the elongated conductive coil.

4. The method of claim 1, further comprising positioning the assembly formed by the elongated conductive coil and the tube in a tubular mold with a diameter substantially equal to an outer diameter of the elongated conductive coil.

5. The method of claim 1, wherein applying the pressure includes applying a radial compression force to an outer surface of the assembly formed by the elongated conductive coil and the tube.

6. The method of claim 1, wherein the polymer material of the tube is polyurethane.

7. The method of claim 1, wherein an outer diameter of the tube is substantially smaller than an inside diameter of the elongated conductive coil.

8. The method of claim 1, wherein an outer diameter of the tube is substantially greater than or equal to an inner diameter of the elongated conductive coil.

\* \* \* \* \*